US009846098B2

(12) United States Patent
Gerbi et al.

(10) Patent No.: US 9,846,098 B2
(45) Date of Patent: Dec. 19, 2017

(54) TOTAL PRESSURE AND TOTAL TEMPERATURE MEASUREMENT IN WET GAS CONDITION

(71) Applicant: Nuovo Pignone Srl, Florence (IT)

(72) Inventors: Filippo Gerbi, Florence (IT); Marco Marrazzo, Florence (IT); Francesco Maraschiello, Florence (IT); Giampaolo Manfrida, Florence (IT)

(73) Assignee: Nuovo Pignone Srl, Florence (IT)

( * ) Notice: Subject to any disclaimer, the term of this patent is extended or adjusted under 35 U.S.C. 154(b) by 232 days.

(21) Appl. No.: 14/653,423

(22) PCT Filed: Dec. 16, 2013

(86) PCT No.: PCT/EP2013/076689
§ 371 (c)(1),
(2) Date: Jun. 18, 2015

(87) PCT Pub. No.: WO2014/095711
PCT Pub. Date: Jun. 26, 2014

(65) Prior Publication Data
US 2015/0346173 A1 Dec. 3, 2015

(30) Foreign Application Priority Data
Dec. 20, 2012 (IT) .............. CO2012A0067

(51) Int. Cl.
*G01N 7/00* (2006.01)
*G01L 19/14* (2006.01)
(Continued)

(52) U.S. Cl.
CPC ............ *G01L 19/14* (2013.01); *G01K 13/028* (2013.01); *G01L 19/0092* (2013.01);
(Continued)

(58) Field of Classification Search
CPC ............ G01N 33/0016; G01L 19/0092; G01L 19/06; G01L 19/14; G01K 13/028; G01F 3/30
(Continued)

(56) References Cited

U.S. PATENT DOCUMENTS 5,025,661 A 6/1991 McCormack
5,433,114 A 7/1995 Cook et al.
(Continued)

FOREIGN PATENT DOCUMENTS

CN 1276059 A 12/2000
CN 102454504 A 5/2012
(Continued)

OTHER PUBLICATIONS

Unofficial English Translation of Chinese Office Action issued in connection with corresponding CN Application No. 201380067280.1 dated May 3, 2016.
(Continued)

*Primary Examiner* — Benjamin Schmitt
(74) *Attorney, Agent, or Firm* — GE Global Patent Operation (57) ABSTRACT

A probe for the measurement of the total pressure or temperature of a two phase wet gas flow is also disclosed. Embodiments provide a stem, a tip on the top of the stem, a cup serving as a shield is formed in the tip, a at least one tube or thermal element positioned within the cup serving as a measuring device for the incoming wet gas flow; at least one hole which passes through at least one wall of the cup; and a pressure changing device configured to accelerate the wet gas flowing around the cup. A method and system for the measurement of the total pressure or temperature of a two phase wet gas flow is also disclosed.

19 Claims, 6 Drawing Sheets

(51) Int. Cl.
*G01N 33/00* (2006.01)
*G01L 19/06* (2006.01)
*G01K 13/02* (2006.01)
*G01L 19/00* (2006.01)
*G01F 1/74* (2006.01)
*G01F 3/30* (2006.01)

(52) U.S. Cl.
CPC .......... *G01L 19/06* (2013.01); *G01N 33/0016* (2013.01); *G01F 1/74* (2013.01); *G01F 3/30* (2013.01)

(58) Field of Classification Search
USPC ........ 73/37, 29.01, 29.03, 31.05, 708, 866.5
See application file for complete search history.

(56) References Cited

U.S. PATENT DOCUMENTS

| | | | |
|---|---|---|---|
| 5,483,838 | A | 1/1996 | Holden |
| 6,609,412 | B2 | 8/2003 | Dimarzo et al. |
| 6,647,777 | B1 | 11/2003 | Kotaka et al. |
| 6,892,584 | B2 * | 5/2005 | Gilkison ............ G01P 5/165 73/1.29 |
| 7,434,470 | B2 | 10/2008 | Engelhardt et al. |
| 7,716,980 | B1 | 5/2010 | Colten et al. |
| 2008/0072979 | A1 | 3/2008 | Rosenbaum et al. |
| 2011/0308311 | A1 | 12/2011 | Dalla et al. |
| 2012/0111100 | A1 | 5/2012 | Tsujii et al. |
| 2012/0279230 | A1 | 11/2012 | Botarelli |

FOREIGN PATENT DOCUMENTS

| | | |
|---|---|---|
| CN | 102725498 A | 10/2012 |
| DE | 102010025898 A1 | 1/2012 |
| FR | 2895076 A1 | 6/2007 |
| GB | 883779 A | 12/1961 |
| GB | 2272296 A | 5/1994 |
| GB | 2272768 A | 5/1994 |
| JP | 6154426 A | 3/1986 |

OTHER PUBLICATIONS

Kovach et al., "Experimental Evaluation by Thermodynamic Methods of Work Input to a Centrifugal Compressor Operating with Water Injection", NACA, Jan. 12, 1951.

Dussourd et al., "A Deceleration Probe for Measuring Stagnation Pressure and velocity of a Particle-laden Gas Stream", Journal of Jet Propulsion, vol. No. 28, Issue No. 1, pp. 24-34, 1958.

Murthy et al., "A Stagnation Pressure Probe for Droplet-laden Air Flow", NASA, vol. No. 12, Issue No. 3, pp. 195-196, Jun. 1986.

Italian Search Report and Opinion issued in connection with corresponding IT Application No. IT CO2012A000067 dated Oct. 10, 2013.

PCT Search Report and Written Opinon issued in connection with corresponding PCT Application No. PCT/EP2013/076689 dated May 8, 2014.

* cited by examiner

TOTAL PRESSURE AND TOTAL TEMPERATURE MEASUREMENT IN WET GAS CONDITION

FIELD OF THE INVENTION

Embodiments of the subject matter disclosed herein generally relate to improvements in wet gas compressor and in particular relates to probes to measure the total temperature and pressure of a hot gas mixed with liquid inside the casing of a compressor.

DESCRIPTION OF STATE OF THE ART

Centrifugal compressors utilized in the extraction of natural gas often must operate in wet gas conditions since the extracted fluid contains a mixture of liquid and gaseous phases. The performances of a centrifugal compressor are modified by the presence in the gas of a liquid phase in the form of liquid droplets dispersed in the main gas flow. Many experiments have been performed on centrifugal compressor under condition of controlled gas humidity and the results show that the performances change with an increased level of the quantity of liquid contained in the gas stream. Therefore normally the liquid components are separated from the gas stream before they enter the compressor. These separator devices require a considerable amount of space and all the separation process is very expensive especially in the case of subsea operations. For this reasons the development of compressors that can operate directly with wet gas without the need of heavy, large and expensive separators is economically very attractive. In the development phase of such type of compressors, the measurements of the main thermodynamic parameters such as flow rate, fluid velocity, total pressure and total temperatures of the gas become very important for the evaluation of their performances. Unfortunately the presence of liquid droplets in the main flow that can reach a percentage in volume of 5%, depending on the gas and liquid topology causes errors in the measurement of some thermodynamic parameters, in particular pressure and temperature, when using conventional instruments, or doesn't allow the measurement at all. This is due to the fact that liquid droplets may deposit on the probe sensitive element giving rise to errors in the measurement. The entrance of the probe may also become clogged due to accumulation of the liquid droplets. Other errors rise from the aerodynamics interaction between droplets and gas with an exchange of quantity of motion that alters the measurement of the real gas pressure. Thus the measurements of thermodynamic parameters in wet gas conditions, in particular inside the casing of a centrifugal compressor, is not an easy task. For what concerns the measurement of temperature the impact of the droplets on the surface of the probe and possible evaporation, drawing heat from the probe surface, results in a temperature reading lower than the true gas temperature. Attempts to measure the pressure and temperature of a wet gas stream relies on methods to prevent the flooding by the liquid of the internal compartment of the probe or to avoid the plugging of the entrance orifice of the probe. The flooding of the probe can be partially resolved by using output orifices. For the plugging the solution found relies on the geometries and on the material employed for the orifice of the probe that can be made using hydrophilic material. In this last solution there is the necessity to substitute the hydrophilic material once is saturated with water. Other solutions foresee probes, in particular of the Pitot type, with particular complicated geometries or rely on the implementation of active systems like the heating of the input orifice to accelerate the droplets evaporation. In any case these or other more complicated solutions are not applicable for use in a centrifugal compressor or work anyway only for a low percentage in mass of the liquid phase. Besides no probe has been found that can be miniaturized to be used for measurements inside a compressor. To this day specific probes that can overcome the described problems have not been developed. Due to the lack of instrumentation able to provide accurate data, measurements of total pressure or total temperature, despite their utility, are not currently carried out during performance tests of compressor operating in wet gas conditions. A miniaturized and reliable probe could be a further step in the development of compressors able to operate in wet gas conditions. The realization of such a probe is therefore highly needed.

BRIEF SUMMARY OF THE INVENTION

Therefore, there is a general need to realize probes that can measure accurately total pressure or total temperature in wet gas condition also at high percentage value of liquid mass in a gas stream. More specifically, there is a need to realize miniaturized probes able to measure total pressure or total temperature in a centrifugal compressor working in wet gas regime.

Therefore, a first aspect of the present invention is a probe.

According to embodiments thereof, a probe for the measurement of the total pressure or the total temperature of a two phase wet gas flow comprises a stem, a tip on the top of the stem, a cup serving as a shield formed in the tip, the cup having a longitudinal axis generally perpendicular to the longitudinal axis of the stem and having an open front end perpendicular to its longitudinal axis by the side of the incoming wet gas flow and a closed back end on the opposite side, at least one tube or one thermal element positioned within the cup serving as pressure or temperature measuring device for the incoming wet gas flow, at least one hole which passes through the walls of the cup, and means to accelerate the wet gas flowing around the cup whereby a pressure depression is created near said at least one hole to suck the liquid, that form a phase of the wet gas flow, from inside the cup.

A second aspect of the present invention is a method to measure total pressure and temperature of a two phase wet gas flow.

According to embodiments thereof, a method to measure total pressure or temperature of a two phases wet gas flow comprises:

using a probe provided with a cup wherein the two phase gas stream can be slow down till at rest, creating a pressure drop around the cup, and sucking the liquid forming one of the two phases from inside the cup through one or more holes formed in the walls of the cup.

In an embodiment, the means to create the pressure drop around the probe consist in at least one nozzle having a longitudinal axis parallel to the longitudinal axis of the cup.

A third aspect of the present invention is a system for measuring the performances of a centrifugal wet gas compressor.

According to embodiments thereof, a system for measuring the performances of a centrifugal wet gas compressor comprises miniaturized probes placed inside the compressor for measuring the total pressure and total temperature of the gas stream laden with droplets of a liquid; the probes are provided with a cup wherein the gas stream can be slow down till at rest and with means to create a pressure drop around the cup in order to suck the liquid droplets from inside the cup through one or more holes formed in the walls of the cup.

BRIEF DESCRIPTION OF THE DRAWINGS

Further characteristics and advantages of the invention will become more apparent at the light of a detailed description of some, but not exclusive, embodiments, illustrated by way of non-restrictive example, with the aid of the accompanying drawings, in which.

DETAILED DESCRIPTION OF THE INVENTION

The following description of exemplary embodiments refers to the accompanying drawings. The same reference numbers in different drawings identify the same or similar elements. The following detailed description does not limit the invention. Instead, the scope of the invention is defined by the appended claims.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

Figure 1:
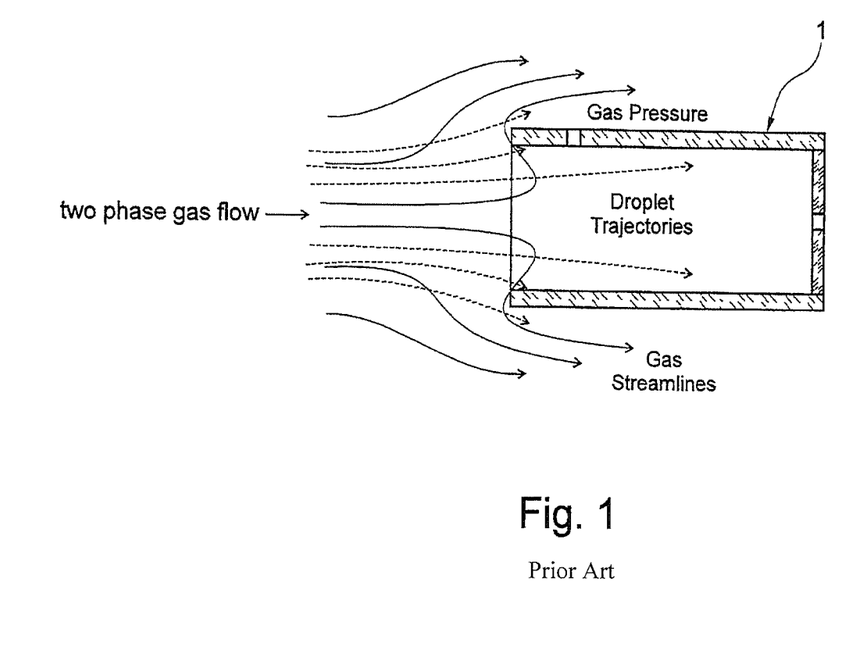
FIG. 1 represents the gas flow lines and the trajectories of the liquid droplets at the entrance of the probe.

FIG. 1 represents (Dussourd Jules L., Shapiro, Ascher H.: "A deceleration probe for measuring stagnation pressure and velocity of a particle-laden gas stream", Jet Propulsion, pages 24-34, January 1957) the complex three-dimensional flow field created by the interaction between the liquid droplets and the gas at the entrance to the probe (1). This interaction is accompanied by an exchange of momentum between the liquid droplets and the flow of gas. The gas pressure in the probe is different from the one that would be measured in the absence of liquid, in fact, it not only increases due to the stagnation point that is created, but also because of the interaction of the gas with the liquid droplets. In general, the liquid droplets have a loss of momentum and this causes an increase of the total pressure in the gas phase. The droplet, because of its greater inertia, tends to continue in a straight line with little change in velocity. Upon crossing the gas streamlines the droplet is subject to a drag force. Both a retarding force and a radially outward force are imposed on the droplet. The droplet not only decelerates, but also migrates away from the axis towards the internal walls of the probe.

In an embodiment of the present invention, the flow of gas is artificially accelerated outside the probe by letting the gas go through a tapered nozzle, having larger dimension at the side facing the incoming gas flow. At the other side the nozzle terminates near a hole, or more, that puts in communication the interior of the probe with the exterior and through this hole the particles of liquid which are located within the probe are sucked outside by the pressure depression thus created.

Figure 2:
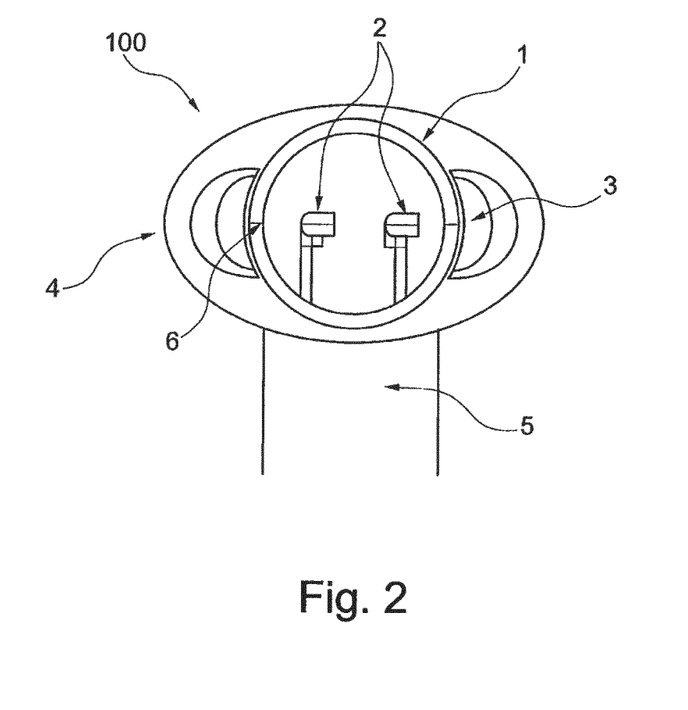
FIG. 2 represents a front view of the probe according to the invention.
Figure 6:
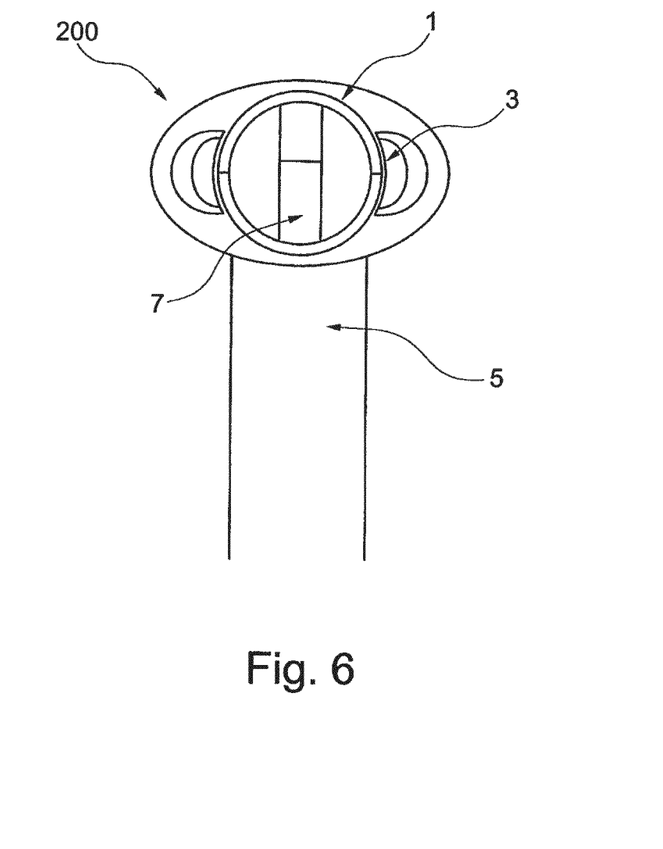
FIG. 6 represents a front view of a probe for measuring the temperature.

With reference to FIG. 2, a probe in accordance with these arrangements is represented. The probe, generally indicated with 100, is seen from the side of the incoming wet gas flow. The probe consists of a stem 5 with a tip 4 on its top. A cup 1, within the tip 4, serving as a shield, opened at the front end and closed at the rear end, will decelerate the wet gas flow creating a zone of stagnation pressure. The measured value of the static pressure of the gas at rest within the cup 1 is equivalent to the value of the total pressure of the gas flow. The static pressure is measured by the tubes 2 positioned inside the cup. Two nozzles 3 on the side of the cup and purging holes 6, of suitable design, through the wall of the cup located at the exit of the nozzle 3, will be able to evacuate the liquid from the cup and at the same time guarantee the necessary pressure recovery needed to perform total pressure measurements. In this embodiment, the tip 4 has the shape of an ellipse and the cup 1 and the nozzles 3 are formed inside the tip 4. As regard the total temperature probe, the purging system is the same. In this case, see FIG. 6, however, a miniaturized shield 7 is used to protect the measuring element from the direct droplets impact. Since the probe cup 1 and the purging hole, or holes, 6 is designed to guarantee the gas temperature recovery, the measured temperature is the total temperature of the gas. The tubes 2 inside the cup 1 are positioned in such a way that their open end is tangential to the gas flow and not adjacent to the cup walls. From inside the cup, the tubes run into the stem till the pressure transducers. Alternatively to pressure tubes, in the stem can be accommodated the temperature sensitive elements and the data collection system, to make a total temperature probe.

Figure 3:
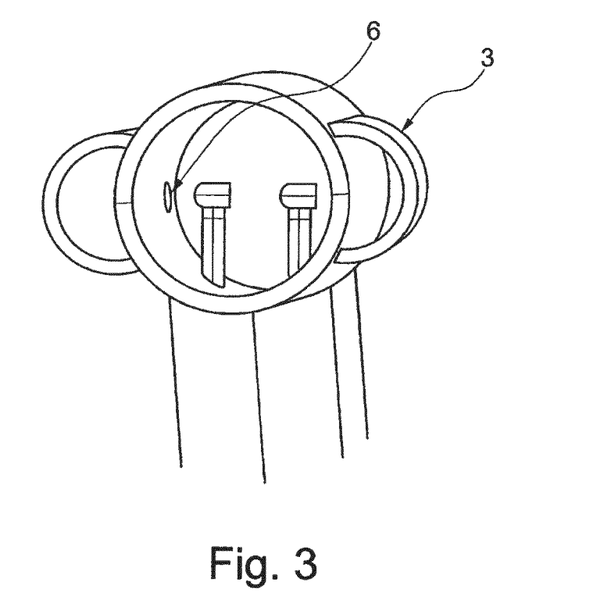
FIG. 3 represents a front view perspective of the probe according to another embodiment.

FIG. 3 shows another embodiment in which the tip 4 is cylindrical and coincide with the cup 1 and two converging nozzles 3 are attached to the external wall of the cup.

Figure 4:
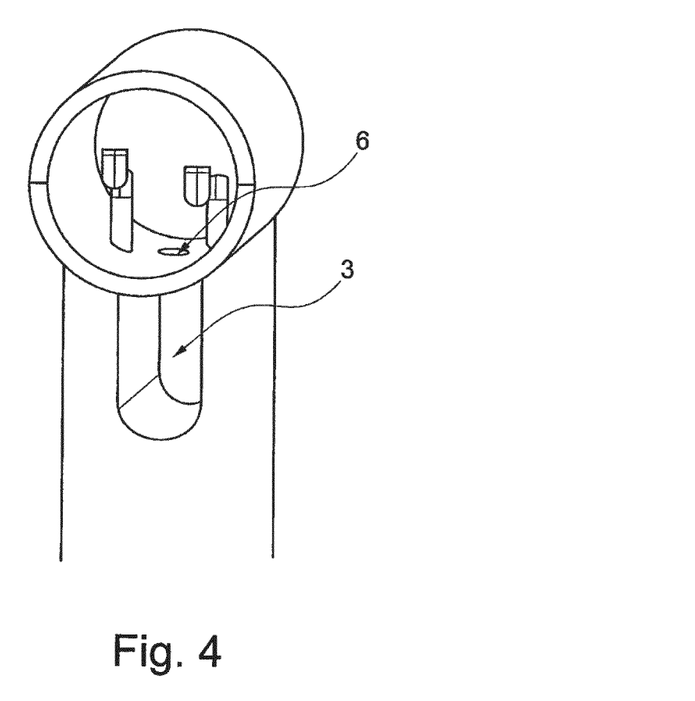
FIG. 4 represents a front view perspective of the probe according to a third embodiment.

FIG. 4 shows another embodiment in which the single nozzle 3 is formed by an aperture in the stem.

Figure 5:
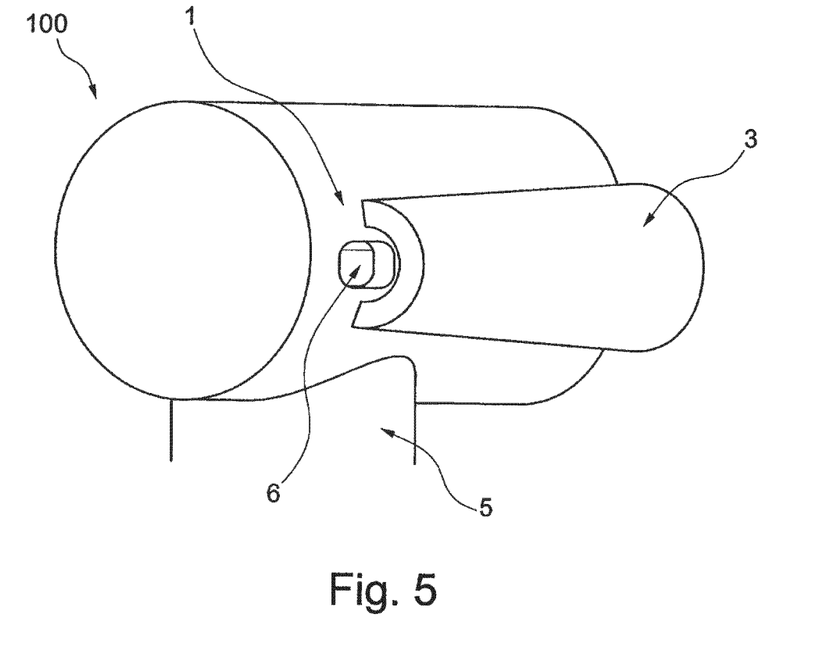
FIG. 5 represents a rear view perspective of the probe showing the tapered nozzle and the purging hole.

FIG. 5 shows a rear view of the probe with in evidence the hole 6 and the nozzle 3. The nozzle has a generally semi conical shape being tapered with decreasing dimension from the entrance of the gas to the exit port in the vicinity of the purging hole 6 where the pressure depression is created.

The geometry of the nozzle can change, but it must guarantee the flow acceleration needed to create depression near purging hole. It is evident that the employment of a nozzle is only a way to obtain the pressure drop, any other arrangements to obtain the same pressure drop in the vicinity of the hole and that is able to suck the liquid from inside the cup falls within the scope of this invention.

Another characteristic of these probes are their dimensions of the order of few millimeter; in this way they can be easily fitted within any suitable measuring place within the compressor. Differently from standard probes, probes according to embodiments of the invention are able to generate a gas expansion on the external side of the cup. This guarantees the appropriate purging of the liquid fraction of the gas flow from the cup, thus making possible a reliable gas total pressure measurement.

The miniaturization of the probes according to embodiments of the invention and their reliability makes them suitable for their use for total pressure and total temperature accurate measurements inside compressors during performances tests in wet gas conditions. Till now this kind of measurements have not been performed during performance tests of wet gas compressors due to absence of instrumentation able to provide accurate data. This invention could be a further step in the development of compressors able to operate in wet gas conditions.

What is claimed is:

1. A probe for the measurement of the total pressure or temperature of a two phase wet gas flow, the probe comprising:
   a stem;
   a tip on the top of the stem;
   a cup serving as a shield is formed in the tip, the cup having a longitudinal axis perpendicular to the longitudinal axis of the stem and comprising an open front end perpendicular to its longitudinal axis by the side of the incoming wet gas flow and a closed back end on the opposite side;
   at least one tube or thermal element positioned within the cup serving as a measuring device for the incoming wet gas flow;
   at least one hole which passes through at least one wall of the cup; and
   a pressure changing device configured to accelerate the wet gas flowing around the cup whereby a pressure depression is created near said at least one hole to suck the liquid, that forms a phase of the wet gas flow, from inside the cup.

2. The probe of claim 1, wherein the pressure changing device comprises at least one nozzle having a longitudinal axis parallel to the longitudinal axis of the cup.

3. The probe of claim 2, wherein the tip is cylindrical and the cup coincide with the tip and the at least one nozzle is positioned adjacent the external surface of the cup, the external surface of the cup forming a wall of the nozzle.

4. The probe of claim 2, wherein the tip is elliptical and the at least one nozzle is formed in the tip, adjacent to the cup, on the side of the major axis of the ellipse.

5. The probe of claim 2, wherein the cup coincides with the tip and the nozzle is formed, adjacent to the cup, in the stem.

6. The probe of claim 2, wherein the at least one nozzle is approximately semi-conical and tapered along its longitudinal axis with the greater aperture on the side of the incoming wet gas flow.

7. The probe of claim 1, wherein for the measurement of total temperature a miniaturized shield is used to protect the measuring device from the direct droplet impact.

8. The probe of claim 1, wherein the at least one tube or thermal element inside the cup is positioned in such a way that its open end is tangential to the gas flow and not adjacent to the at least one wall of the cup and comprises a part running into the stem parallel to the longitudinal axis of the stem.

9. The probe of claim 1, wherein the at least one tube or thermal element connects its open end with transducers and a data collection system at the end of the stem.

10. A method to measure total pressure and temperature of a two phase wet gas flow, the method comprising:
    using a probe provided with a cup wherein the two phase wet gas flow can be slowed down until the two phase wet gas flow is at rest;
    creating a pressure drop around the cup through a pressure changing device; and
    sucking the liquid forming one of the two phases from inside the cup through one or more holes formed in at least one wall of the cup.

11. A system for measuring the performances of a centrifugal wet gas compressor, the system comprising:
    miniaturized probes placed inside the compressor for measuring the total pressure and total temperature of the gas stream laden with liquid droplets, the probes comprising:
      a cup wherein the gas stream can be slowed down until the gas stream is at rest; and
      a pressure changing device configured to create a pressure drop around the cup in order to suck the liquid droplets from inside the cup through one or more holes formed in at least one wall of the cup.

12. The system of claim 11, further comprising a tip, wherein the tip is cylindrical and the cup coincides with the tip and at least one nozzle is positioned adjacent the external surface of the cup, the external surface of the cup forming a wall of the nozzle.

13. The system of claim 12, wherein the at least one nozzle is approximately semi-conical and tapered along its longitudinal axis with the greater aperture on the side of the incoming wet gas flow.

14. The system of claim 11, further comprising a tip, wherein the tip is elliptical and the at least one nozzle is formed in the tip, adjacent to the cup, on the side of the major axis of the ellipse.

15. The system of claim 11, further comprising a tip, wherein the cup coincides with the tip and the at least one nozzle is formed, adjacent to the cup, in a stem.

16. The system of claim 11, wherein for the measurement of total temperature a miniaturized shield is used to protect the measuring device from the direct droplet impact.

17. The system of claim 11, wherein the at least one tube or thermal element inside the cup is positioned in such a way that its open end is tangential to the gas flow and not adjacent to the at least one wall of the cup and comprises a part running into a stem parallel to the longitudinal axis of the stem.

18. The system of claim 11, wherein the at least one tube or thermal element connects its open end with transducers and a data collection system at the end of a stem.

19. The system of claim 11, wherein the pressure changing device comprises at least one nozzle having a longitudinal axis parallel to the longitudinal axis of the cup.

* * * * *